United States Patent [19]

Fike et al.

[11] Patent Number: 5,126,269
[45] Date of Patent: Jun. 30, 1992

[54] SPIN FILTER PERFUSION BIOREACTOR (SFPB) CELL CULTURE APPARATUS

[75] Inventors: Richard Fike, Clarence; Stefan Weiss, Grand Island, both of N.Y.; Patrick Pomeroy, Concord, Calif.

[73] Assignee: Life Techologies, Inc., Gaithersburg, Md.

[21] Appl. No.: 581,706

[22] Filed: Sep. 13, 1990

[51] Int. Cl.⁵ .............................................. C12M 3/00
[52] U.S. Cl. .................................... 435/284; 435/286; 435/311; 435/312; 435/313; 435/314; 435/315
[58] Field of Search ............... 435/316, 813, 283, 284, 435/285, 286, 311-315; 422/269, 270, 271; 277/186, 187, 12; 210/232, 383, 450

[56] References Cited

U.S. PATENT DOCUMENTS

| | | |
|---|---|---|
| 3,172,235 | 3/1965 | Bjorklund . |
| 3,186,917 | 4/1962 | Gerhardt et al. ........................ 195/1 |
| 3,647,632 | 4/1968 | Johnson et al. . |
| 4,535,062 | 8/1985 | Muller ................................. 435/289 |
| 4,649,118 | 3/1987 | Anderson . |

FOREIGN PATENT DOCUMENTS 0317874  5/1989  European Pat. Off. .

OTHER PUBLICATIONS

S. A. Weiss et al., "*Cell Culture Methods for Large-Scale Propagation of Baculoviruses*", 1986.
The Virtis Company, Gardiner, N.Y., Technical Catalog for Product (Model #240887) entitled "*Virtis Biospin Dynamic Filter*", 2 color sheets, date of publication is unknown.
S. A. Weiss et al., "*Techniques in Setting Up and Maintenance of Tissue and Cell Cultures*", Techniques in the Life Sciences, C110, (1985), (16 pages).

*Primary Examiner*—Robert J. Warden
*Assistant Examiner*—Matthew W. Hanley
*Attorney, Agent, or Firm*—Sterne, Kessler, Goldstein & Fox

[57] ABSTRACT

An apparatus is disclosed that separates and removes to an external source, spent cell culture media from a cell culture media and cell culture mixture. The apparatus generally comprises a culture vessel, a filter member, wherein the filter member is positioned in the culture vessel to form an outside region and an inside region. Further provided is a tube member. The tube member being positioned in the inside region and having an opening therein to thereby remove the spent cell culture media brought into the inside region. Further disclosed is a structure for rotating the filter member around the tube member and a structure for sealing the outside region from the inside region when the filter member is rotating around the tube member.

7 Claims, 3 Drawing Sheets

SPIN FILTER PERFUSION BIOREACTOR (SFPB) CELL CULTURE APPARATUS

BACKGROUND OF THE INVENTION

1. Field of the Invention

The present invention relates generally to bioreactors for growing cultures. More particularly, the present invention relates to a bioreactor employing spin filter perfusion technology.

2. Related Art

Traditional methodologies for culture of suspension cells include batch culture, fed batch culture and chemostat culture. All of these methods do not allow for concentration of cells within the culture vessel. In these systems, maximal cell yield is limited by the fact that nutrients in the growth medium become depleted and waste products increase to deleterious levels. For many suspension cell types, this allows for growth slightly above $10^6$ cells/mL. Suspension cells that produce a biological product often demonstrate maximum production when the cells have achieved their peak density. Unfortunately, at this point, many of the nutrients necessary for production of the biological are already depleted.

Replacing the supernatant with fresh medium while containing the cells within the bioreactor would be advantageous not only for cell growth but also for yield of the biological product. This would also allow for an efficient continuous culture that could be maintained over long periods of time with lower cell turnover rates as compared to chemostat culture. By keeping a low cell turnover rate, the selection pressures should be much reduced and energy and materials could be turned toward production of product as opposed to cell growth.

Such cell concentration is possible using several methodologies to include hollow fiber cell concentration, external centrifuges, and spin filter perfusion technology.

Hollow fiber units can be used to concentrate cells in a culture while perfusing nutrients through the culture. Cells and media pass through the inner capillary spaces where spent culture media (but not cells) pass across the fiber to the extra-capillary space. Cells are inhibited by passing due to fiber pore size. Fresh medium is then added to the bioreactor elsewhere. However, change to a different cell type results in need to recalibrate perfusate/retentate flow rates to prevent plugging. Also, pump shear forces on the cell culture passing through the hollow fiber may be significant since flow rate must be significant to prevent cells becoming trapped against the sides of the inner fiber wall.

Use of an external centrifuge to concentrate cells in a culture has been advocated but has practical drawbacks such as expense and complexity of design.

Biospin cell concentration as a means of perfusing cultures has been advocated for several years. Biospin cell concentration is described generally in *Spin Filter Culture: The propagation of Mammalian Cells in Suspension*, Himmelfarb et al., Science 164: 555-557, 1969). This technology generally consists of a mesh filter spinning around a tube. The spinning of the filter causes spent culture medium to pass through the filter and into the tube where it is removed to an external collection vessel.

Conventional spin filter units, however, have several significant disadvantages. Conventional spin filter units do not provide sealing as the filter rotates about the tube. Having no seal results in cell culture entering the tube during spinning and/or the introduction of air into the tube which thereby limits the perfusion rate. Limiting the perfusion rate significantly affects cell yield due to not being able to perfuse enough cell culture medium to satisfy a high density culture.

Further, conventional spin filter units have a relatively complex internal structure, making capacity scaleup or scale-down, assembly and disassembly, and sterilization difficult. Scale-up and or scale-down in particular, is a very desirable feature for perfusion processing operations.

SUMMARY OF THE INVENTION

The present invention is a bioreactor that uses spin filter technology. The bioreactor of the present invention solves the problems inherent in conventional spin filter based bioreactors. The bioreactor of the present invention further provides features heretofore unavailable in conventional spin filter bioreactors.

The bioreactor of the present invention generally comprises a culture vessel for storing small or large quantities of cell culture and cell culture medium. The present invention further comprises a cylindrical mesh filter. As such, spent liquid but not cells can pass through. The filter when positioned in the culture vessel forms an inside region and an outside region.

The present invention further comprises a tube member. The tube member is positioned in the inside region and has an opening located at the bottom of the tube. The opening allows the spent cell culture media brought into said inside region to be removed to an external collection vessel.

The present invention further comprises first means for rotating the filter around the tube member. Rotation of the filter member with pump (suction) action causes the spent cell culture media to pass from the outside region through the mesh and into the inside region. The rotating means comprises an upper bushing. The upper bushing is rotatably mounted on a retainer clip mounted on the tube member. The filter is mounted to the upper bushing. The rotating means further comprises a magnetic stir bar. The magnetic stir bar is attached to the filter. Upon actuation from an external magnetic stirring table, the stir bar and thus the filter are caused to rotate.

The present invention further comprises second means for sealing the outside region from the inside region except for communication through the mesh. The sealing means comprises a first o-ring. The first o-ring is positioned around the tube member to thereby provide frictional contact with the tube member. The sealing means further comprises a retainer member. The retainer member is provided to force the first o-ring into and out of frictional contact with the tube member. The frictional contact between the first o-ring and the tube member may be increased or decreased by the tightening or loosening of the retaining member.

BRIEF DESCRIPTION OF THE DRAWINGS

The following detailed description will be more fully understood with reference to the accompanying drawings in which.

DETAILED DESCRIPTION OF THE PREFERRED EMBODIMENTS

Figure 1:
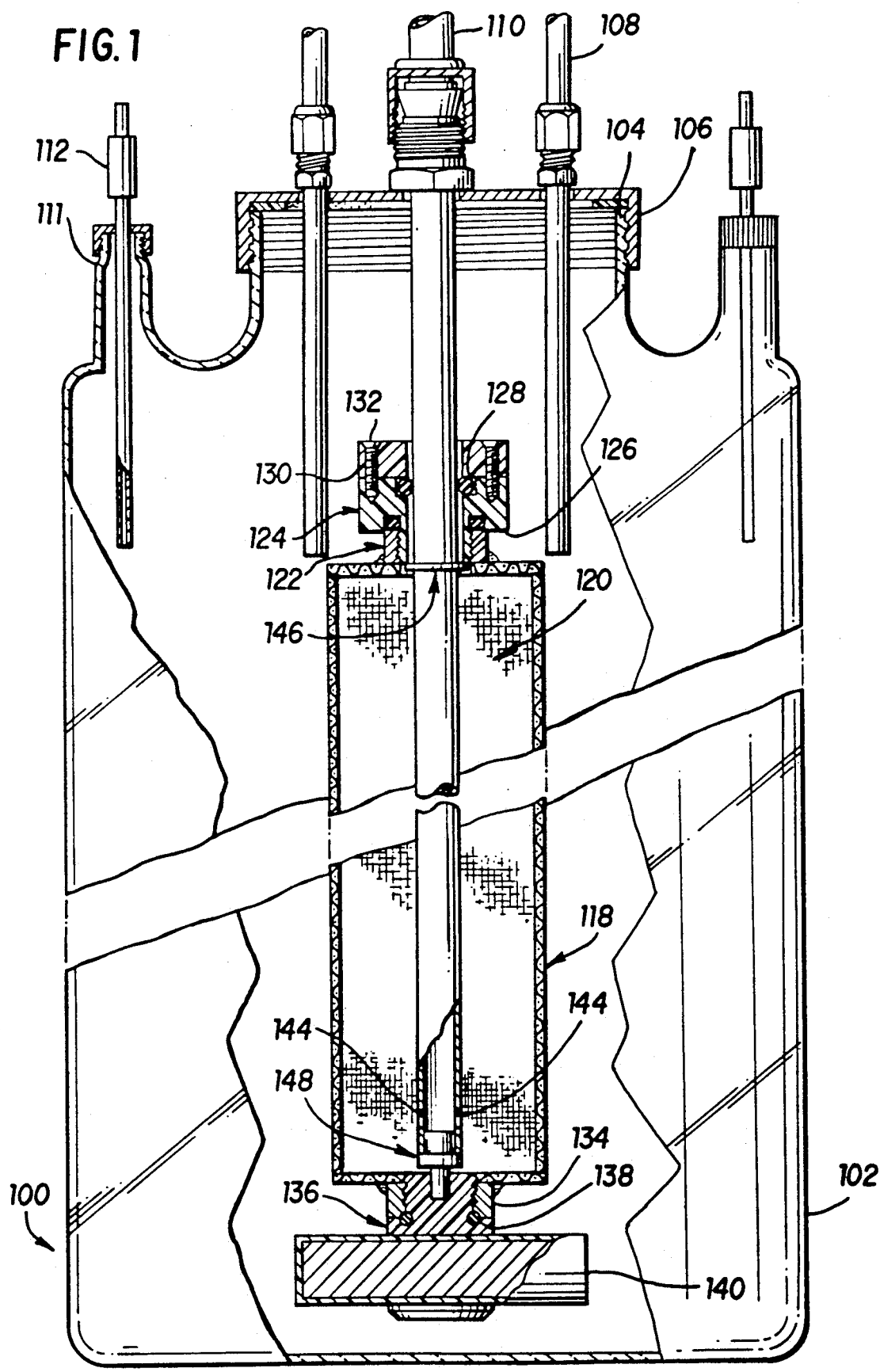
FIG. 1 is a cross-sectional assembled view of the present invention.

Referring now to FIG. 1, wherein the bioreactor 100 of the present invention is shown. Bioreactor 100 first comprises a culture vessel 102. Culture vessel 102 is generally provided to contain the cell culture and cell culture media.

Culture vessel 102 is formed to have a threaded neck 104. Threaded neck 104 is provided to securely engage with corresponding threads on a cap 106.

Cap 106 is provided to enclose the culture vessel 102 and mount a plurality of conduits 108 and a tube 110 (to be described). Cap 106 is of conventional design and is made of 316-L stainless steel.

As will be more fully discussed herein, tube 110 is provided to remove the spent cell culture medium. Conduits 108 and tube 110 are secured to the cap 106 with conventional mounting techniques.

Culture vessel 102 is further formed to have a plurality of ports 111. Ports 111 are provided to receive test probes 112. Test probes 112 are provided for testing parameters such as the pH and DO of the cell culture media. Test probes 112 are mounted to ports 110 using conventional mounting techniques.

In the preferred embodiment, culture vessel 102 has a 14-liter capacity and is made of glass. Glass is the preferred material because it is compatible with common sterilization techniques such as moist heat sterilization (autoclaving). Sterilization is important so that the cell culture and cell culture media contained in culture vessel 102 will not become contaminated.

Culture vessel 102, however, can be made from a variety materials such as stainless steel. As culture vessel 102 increases in capacity for large scale perfusion applications (100 liters), stainless steel may become the material of choice due to its durability and resistance to breaking.

Bioreactor 100 of the present invention further comprises a filter 118. Filter 118 is a cylinder shaped member and when placed inside the culture vessel 102, forms an inside region (area inside filter 118) and an outside region (area outside the filter 118). Filter 118 is further formed to have a mesh structure 120 that allows communication between the inside region and the outside region. The mesh 120 of the preferred embodiment has a porosity of 5μ. Mesh 120, however, may be of a different size, smaller or larger. As such, liquid but not cells will pass through.

Filter 118 of the preferred embodiment is a one piece component available in variety of lengths, diameters, and mesh porosities. Filter 118 is further made from 316-L stainless steel. This material is preferred because of chemical durability and ability to sterilize.

Filter member 118 is commercially available from Pall Porous Metals Filter Company, product No. MBS 1001P05, Cortland, NY. As will be discussed more fully herein, the commercial availability of the filter 118 in a variety of lengths, diameters, and mesh porosities provides significant flexibility over conventional spin filter based bioreactor units, in that the perfusion rates and volumes can be easily scaled up or down by replacement of the filter 118.

Further shown by FIG. 1 is an upper end fitting 122. Upper end fitting 122 is provided as a means for securing filter 118 to an upper bushing 124 (to be described). Upper end fitting 122 is formed with an opening (not labeled) such that the tube 110 (to be described) can freely rotate therein. One end of upper end fitting 122 is welded to the top end of filter 118. The other end of upper end fitting 122 has threading provided therein for engagement with the upper bushing 124 (to be described).

Upper end fitting 122 of the preferred embodiment is made of 316-L stainless steel. Upper end fitting 122 can likewise be made by a variety of manufacturing processes.

Upper bushing 124 is provided to allow filter member 118 (attached thereto) to sealably rotate about the tube 110. Upper bushing 124 has formed therein a first cylindrical recess (not labeled) to receive a lower o-ring 126.

Lower o-ring 126 is provided to ensure a liquid tight seal when the first end fitting 122 and upper bushing 124 are attached. When upper bushing 124 is screwed into upper end fitting 122, lower o-ring 126 is caused to elongate and provide a seal for the upper bushing 124 and upper end fitting 122 connection.

In the preferred embodiment lower o-ring is made of silicon. Lower o-ring 126, however, can be easily replaced with other suitable materials and/or sealing means such as sealing paste or the like. Such sealing paste may for example be applied to the threads of the upper bushing 124.

Further shown is an upper o-ring 128. Upper o-ring 128 functions to seal the inside region of filter 118 from the outside region of filter 118 as filter 118 rotates about the tube 110. The upper o-ring 128 prevents the fluid and cells from entering the inside region of the filter 118 (only spent cell culture media should be allowed to enter the inside region via mesh 120). This is a significant feature.

Upper o-ring 128 is suitably mounted within a circular recess (not labeled) in the upper surface of the upper bushing 124. Upper o-ring 128 is securely retained by a retainer member 130. Retainer member 130 securely fastens to upper bushing 124 with a plurality of screws 132. As the retainer member 130 is tightened onto the upper bushing 124, the upper o-ring 128 is caused to elongate causing a friction sealable contact between the upper o-ring 128 and the tube 110.

Increasing or decreasing this friction contact also provides an additional benefit: increased friction contact makes rotation more difficult while decreased friction contact makes rotation easier. The ability to adjust the rotational friction (speed) of the filter 118 is a significant feature of the present invention. However, care must be taken to avoid making the upper o-ring 128 too loose because culture cells may pass from the outside region of the filter 118 into the inside region.

Upper o-ring 128 is made of silicon. Upper o-ring 128, like lower o-ring 126, can be readily purchased from a variety of sources. It should also be noted that upper o-ring 128 can take a variety of other shapes, and be made from other materials. Furthermore, other sealing means can be readily employed to provide the same sealing function while the filter 118 is rotating about the tube 110. Such alternative sealing means may be that of a conventional mechanical seal employing carbon surface and ceramic contact surfaces.

The bioreactor 100 of the present invention further comprises a lower end fitting 134. Lower end fitting 134 is provided to completely enclose the bottom of filter 118 and to secure a lower bushing 136 (to be described). Lower end fitting 134, like upper end fitting 122, is welded to filter 118.

Further shown is a stir bar o-ring 138. The stir bar o-ring 138 is mounted in a recess formed in the lower bushing 136. When the lower bushing 136 is screwed into the lower end fitting 134 by conventional threading means, the stir bar o-ring 138 becomes elongated, creating a sealed lower bushing 136/lower end fitting 134 connection.

Bioreactor 100 of the present invention further comprises a stir bar 140. Stir bar 140 is a magnetic cylindrical bar securely mounted by conventional connecting means with lower bushing 136. Stir bar 140 is made from conventional material 142 having appropriate magnetic properties. Stir bar 140 has an external coating 143 that encapsulates the magnetic material 142 to among other things, prevent contamination.

As will be more fully shown, upon application of an external magnetic device (not shown), stir bar 140 is caused to rotate thereby causing lower end fitting 136 and filter 118 to rotate. Rotation of filter 118 with pump (suction) action within culture vessel 102 causes spent cell culture media to pass through the mesh 120 and into the inside region of filter 118.

In one embodiment, spin filter assembly 120 rotates at speeds of 100 and 150 rpm. Results obtained at these speeds indicate that no development of shear forces strong enough to inhibit cell growth will occur. The ability of the present invention to operate at these speeds without the development of shear stresses is a significant advantage of the present invention over conventional spin filter units. It should be understood that the bioreactor unit 100 can easily operate at slower or faster speed than hereto identified.

As has been previously identified, bioreactor 100 of the present invention comprises the tube 110. Tube 110 functions to remove the spent cell culture media separated by rotation of the filter 118. Tube 110 extends outside the culture vessel 102 to an external collection source (not shown). Tube 110 is formed with a plurality of openings 144 (better viewed in FIG. 3 to be described herein). Openings 144 are provided to allow the spent culture medium to enter tube 110.

Tube 110 is of conventional design and is made from 316-L stainless steel. The 316-L stainless steel material is the preferred choice because it is compatible with common sterilization techniques. Tube 110 can be readily purchased from a variety of manufacturers.

The bioreactor 100 of the present invention further comprises a retainer clip 146. Retainer clip 146 is fixably mounted in a recessed groove (not shown) formed in tube 118. Retainer clip 146 is provided to act as a rotating bearing surface for the lower end of upper bushing 124. As will be shown more clearly herein, in operation, upper bushing 124 is being supported by and rotating on, retainer clip 146. Therefore, retainer clip 146 must be strong and durable to withstand the weight of the upper bushing 124 and all parts attached to the upper bushing, such as the filter 118. Retainer clip 146 can be readily purchased from a variety of manufacturers.

Further provided is a guide pin 148. Guide pin 148 is securely mounted to the lower end of tube 110. Guide pin 148 is provided to rotatably secure the tube 110 in the center of the filter 118. Guide pin 148 is freely mounted in a recess (not labelled) formed in the top surface of lower bushing 136.

Guide pin 148 is made of teflon. Guide pin can be purchased from a variety of manufacturers or machined form fitted.

Figure 2:
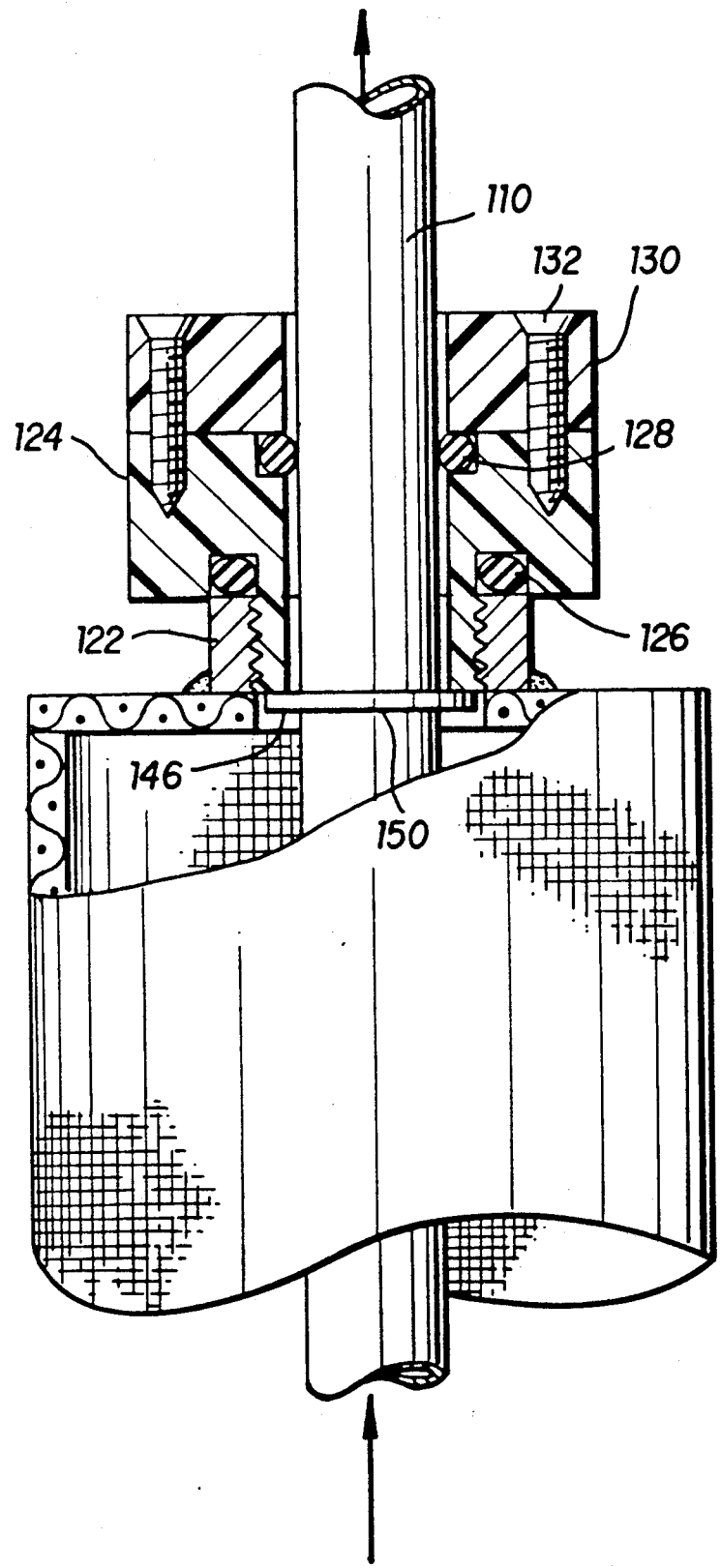
FIG. 2 is an enlarged view of FIG. 1 showing the upper assembled end of the spin filter of the present invention.

Referring now to FIG. 2, wherein an enlarged view showing the assembly and operation of the first end fitting 122, upper bushing 124, upper o-ring 128, lower o-ring 126, tube 110, and retainer clip 146. As shown, the bottom surface of upper bushing 124 is resting on retainer clip 146. Retainer clip 146 is securely fixed in tube 110 by a recessed groove 150 formed in tube 110. As filter 118 is caused to rotate, so is upper bushing 124. As upper bushing 124 rotates, it can be readily seen that upper o-ring 128 remains in sealable contact with tube 110. This sealable contact prevents leakage of cell culture into the inside region of filter 118. Furthermore, this sealable contact causes a resistance to rotation. Resistance to rotation can be increased by providing a larger o-ring or by tightening the force exerted by retaining member 130 via screwing of screws 132. Resistance to rotation can be decreased by loosening retainer member 130.

Figure 3:
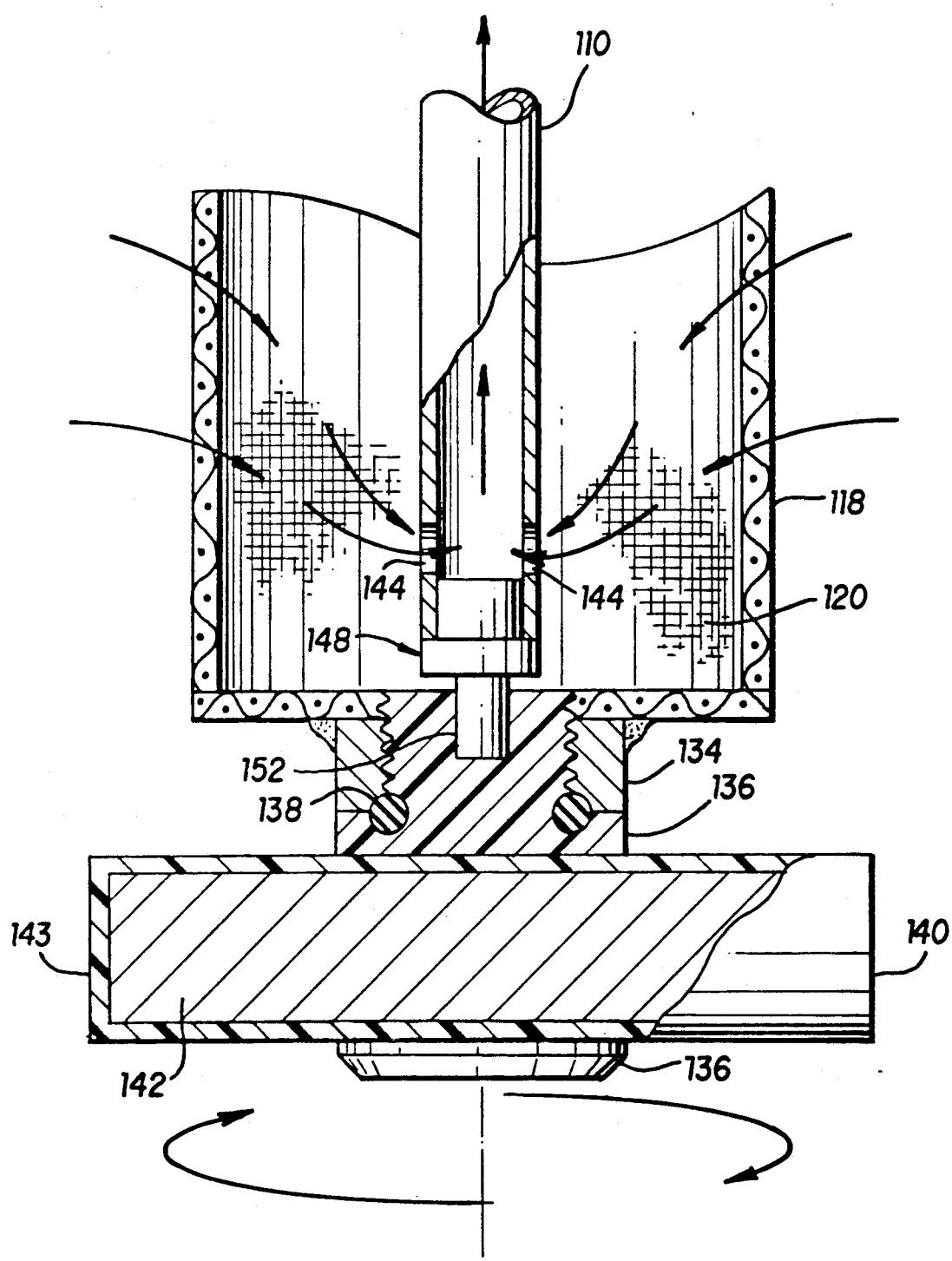
FIG. 3 is an enlarged view of FIG. 2 showing the lower assembled end of the spin filter of the present invention.

Referring now to FIG. 3, wherein an enlarged view showing the lower end of filter 118/lower end of tube 110 interface. As shown, upon rotation of magnetic stir bar 140, lower bushing 136 and thus filter 118 are caused to rotate. Upon rotation, guide pin 148 being rotatably positioned in recess 152 remains stationary. As indicated by the directional arrows, rotation of filter 118 with pump (suction) action causes spent culture medium to enter through the mesh 120 of filter 118 and into the internal region. Thereafter, upon activation of an external pump (not shown), the spent culture medium is caused to flow into openings 144 and up tube 110 where it is removed to an external collection vessel (not shown).

The bioreactor 100 of the present invention has several significant advantages over conventional bioreactors. One such advantage is that bioreactor 100 will perfuse larger volumes of media from high density cell cultures for longer periods of time than conventional spin filter units. This is because filter 118 has a seal tight design as it rotates about tube 110 thereby ensuring that only spent cell culture medium and not cell culture enter tube 110.

Perfusion of larger volumes of media from high density cell cultures is also due to minimal "plugging" of filter 118. It is known in the field that one of the limiting problems with conventional spin filter units is "plugging" when cell density begins to increase. Plugging is caused by the action of cells becoming entrapped in the porous mesh and preventing spent culture medium from passing therein. One reason why the bioreactor 100 of the present invention has much less propensity toward plugging compared to conventional units is because in the present invention, the filter 118 can be scaled-up with a larger capacity culture vessel 102. Scaling up or down in the present invention is performed by replacing filter 118 with one of different length and/or diameter. The present invention allows the user to specify any desired surface area per liter volume of culture. Conventional spin filter devices do not have this capability due to their complex designs.

Moreover, the present invention allows for spinning of the filter 118 while maintaining a seal between the culture and the removed media (filtrate). This is essential when perfusing large volumes of media from high density cell cultures. The sealing means of the present invention is simple and can easily be assembled and disassembled.

Furthermore, the sealing means of the present invention can be tightened so as to diminish the freedom of rotation of filter 118. Likewise, the sealing means can be loosened so as to increase the freedom of rotation of filter 118. This is valuable for one can maximize the seal dependent on the external device driving the magnetic stir bar 140.

The foregoing description is intended primarily for purposes of illustration. The bioreactor 100 of the present invention may be embodied in other forms or carried out in other ways without departing from the spirit or scope of the invention. Modifications and variations still falling within the spirit or the scope of the invention will be readily apparent to those of skill in the art.

Such modifications may include altering size, shape, and/or porosity of filter 118. Other modifications include using alternative materials to fashion the spin filter perfusion bioreactor. Still further modification may comprise using multiple bioreactor units in a series/parallel design or using multiple spin filter units in series and/or parallel in the same or multiple bioreactors.

What is claimed is:

1. A bioculture apparatus for separating and removing to an external collection vessel spent cell culture media from a cell culture media and cell culture mixture, which apparatus comprises:
   (a) a culture vessel having a closed end portion, side walls extending from said closed end portion, and a neck portion extending from said side walls and having a neck opening to permit access to the interior of said vessel;
   (b) a filter member having an annular disk top portion, an annular disk bottom portion, and a mesh portion disposed longitudinally between said annular disk top portion and said annular disk bottom portion, said filter member, when positioned in said culture vessel, forming an inside region within said filter member and an outside region defined between said filter member and said side walls of said culture vessel;
   (c) a tube member having a distal portion extending into said culture vessel, said tube member defining an axis of rotation, said tube member passing through said annular disk top portion of said filter member and into said inside region, said distal portion of said tube member having an opening disposed within said inside region through which the spent cell culture media brought into said inside region may be removed;
   (d) means for rotating said filter member about said axis of rotation defined by said tube member whereby the spent cell culture media from said outside region is caused to pass through said mesh into said inside region where it can be removed via said opening in said distal portion of said tube member; and
   (e) means for sealing said outside region from said inside region except for communication through said mesh, said means for sealing including a bushing attached to said annular disk top portion of said filter member, a retainer member, and a first O-ring, said bushing having a first surface and having a first cylindrical bore passing therethrough, said retainer member having a second surface adapted to engage with said first surface of said bushing and having a second cylindrical bore passing therethrough, said first O-ring being positioned around said tube member to thereby provide frictional contact with said tube member, said first and second cylindrical bores being adapted to accept passage of said tube member such that said first O-ring may be sandwiched between said first and said second surfaces to thereby force said first O-ring into and out of frictional contact with said tube member while still allowing rotation of said filter member relative to said tube member.

2. A bioculture apparatus as claimed in claim 1, wherein said rotating means further comprises a retainer clip mounted on said tube member, said bushing rotatably resting on said retainer clip.

3. A bioculture apparatus as claimed in claim 2, wherein said rotating means further comprises a magnetic stir bar, said magnetic stir bar being attached to said filter member.

4. A bioculture apparatus as claimed in claim 1, wherein said first o-ring is disposed within a circular recess formed in said bushing.

5. A bioculture apparatus as claimed in claim 4, wherein said bushing is attached to said annular disk top portion of said filter member by a threaded end fitting which is fixedly attached to said annular disk top portion of said filter member, a second O-ring provides a sealable connection between said threaded end fitting and said bushing.

6. A bioculture apparatus for use with a culture vessel having a closed end portion, side walls extending from said closed end portion, and a threaded open neck portion extending from said side walls for separating and removing to an external collection vessel, spent cell culture media from a cell culture media and cell culture mixture, said bioculture apparatus comprising:
   (a) a cap adapted to be mounted to the threaded neck opening of the culture vessel;
   (b) a tube member attached to said cap such that when said cap is mounted to said threaded neck opening of the culture vessel a distal portion of said tube member will extend downwardly into the culture vessel, said tube member defining an axis of rotation and having an outlet opening disposed in said distal portion through which the spent cell culture media may be removed from the culture vessel;
   (c) a substantially cylindrical filter member rotatably coupled to said tube member, said filter member having a filter opening adapted to allow entry of said tube member into said filter member such that said outlet opening in said tube member is positioned within said filter member and such that said filter member is substantially free to rotate on said tube member about said axis of rotation, said filter member being adapted for use with the culture vessel such that when said cap is mounted to said threaded neck opening of the culture vessel, said filter member forms an inside region within said substantially cylindrical filter member and an outside region between said substantially cylindrical filter member and the side walls of the culture vessel;
   (d) magnetic means for rotating said filter member about said axis of rotation defined by said tube member whereby the spent cell culture media from said outside region is caused to pass through said filter member into said inside region where it can be removed via said outlet opening in said tube member; and (e) means for sealing said outside region from said inside region except for communication through said filter member, said means for sealing including a bushing attached to said filter member at said filter opening, a retainer member, and a first O-ring, said bushing having an upper surface and having a first cylindrical bore passing therethrough, said retainer member having a lower surface adapted to engage with said upper surface of said bushing and having a second cylindrical bore passing therethrough, said first O-ring being positioned around said tube member to thereby provide frictional contact with said tube member, said first and second cylindrical bores being adapted to accept passage of said tube member such that said first O-ring may be sandwiched between said upper surface and said lower surface to thereby force said first O-ring into and out of frictional contact with said tube member while still allowing rotation of said filter member relative to said tube member.

7. The bioculture apparatus set forth in claim 6, wherein said rotating means further comprises a retainer clip mounted on said tube member, said bushing rotatably resting on said retainer clip.

* * * * *